United States Patent
Vito et al.

(10) Patent No.: US 9,241,821 B2
(45) Date of Patent: Jan. 26, 2016

(54) JOINT DECOMPRESSION DEVICES

(75) Inventors: Guarino Vito, Glen Rock, NJ (US);
Paul Duffy, Verona, NJ (US)

(73) Assignee: GD Ortho LLC, Glen Rock, NJ (US)

( * ) Notice: Subject to any disclaimer, the term of this patent is extended or adjusted under 35 U.S.C. 154(b) by 469 days.

(21) Appl. No.: 13/270,375

(22) Filed: Oct. 11, 2011

(65) Prior Publication Data
US 2013/0090584 A1 Apr. 11, 2013

(51) Int. Cl.
*A61H 1/00* (2006.01)
*A61H 1/02* (2006.01)
*A61F 5/01* (2006.01)

(52) U.S. Cl.
CPC ............. *A61F 5/0125* (2013.01); *A61H 1/024* (2013.01); *A61H 1/0277* (2013.01); *A61H 1/0288* (2013.01); *A61H 2201/1253* (2013.01)

(58) Field of Classification Search
CPC ... A61H 1/024; A61H 1/0277; A61H 1/0288; A61F 5/0125
USPC ............. 601/5, 23, 33, 34, 40, 112, 118–125, 601/134–137, 147; 602/5, 23–26, 62; 128/882
See application file for complete search history.

(56) References Cited

U.S. PATENT DOCUMENTS

| | | | | |
|---|---|---|---|---|
| 2,179,903 A | * | 11/1939 | Spears | 602/26 |
| 2,270,685 A | * | 1/1942 | Miller | 602/62 |
| 4,572,170 A | * | 2/1986 | Cronk et al. | 602/26 |
| 4,628,918 A | * | 12/1986 | Johnson, Jr. | 602/13 |
| 5,133,341 A | * | 7/1992 | Singer et al. | 602/16 |
| 5,207,637 A | * | 5/1993 | Janke et al. | 602/26 |
| 5,267,946 A | * | 12/1993 | Singer et al. | 602/16 |
| 5,417,647 A | * | 5/1995 | Down | 602/26 |
| 5,501,659 A | * | 3/1996 | Morris et al. | 602/27 |
| 7,645,217 B2 | * | 1/2010 | Habing et al. | 482/140 |
| 8,376,974 B2 | * | 2/2013 | Nace | 602/16 |

* cited by examiner

*Primary Examiner* — Justine Yu
*Assistant Examiner* — Kathrynn Reilly
(74) *Attorney, Agent, or Firm* — Bakos & Kritzer (57) ABSTRACT

An apparatus for treating a human knee, such as a knee decompression apparatus or device, is described. In some examples, the apparatus includes a bolster, one or more support bars configured to place the bolster proximate to the popliteal fossa of the knee, and one or more straps or other attachment devices configured to removably attach the apparatus to the knee (or, area of the leg that includes the knee) of a patient.

19 Claims, 8 Drawing Sheets

JOINT DECOMPRESSION DEVICES

BACKGROUND

Conventional medical care with respect to knee ailments and other joint ailments, such as arthritis, pain, meniscus tears, and others, often requires time consuming and costly treatments requiring numerous and routine patient visits to doctors, physical therapists, and other specialists. Typical treatments of osteoarthritis and other joint ailments may involve medication (e.g., analgesics), lifestyle modifications (e.g., restriction from certain activities), surgeries (e.g., joint replacements), physical therapy and so on. For example, a patient may work with a physical therapist in order to relieve pain or strengthen muscles around an ailing joint.

Although these treatments may alleviate suffering in a patient, they can be intrusive, time consuming, and, unfortunately in many instances ultimately ineffective. Further, typical treatments often seek to alleviate pain (e.g., medication) or remove the objects causing pain (e.g., joint replacements), rather than the making the appropriate adjustments, corrections, or modifications that may lead to the healing or improvement of affected and painful areas.

The most common device for facilitating the healing of various joints is a brace, or in a more primitive form, a splint. For example, there are many different types of knee and elbow braces that stabilize surrounding muscles in order to facilitate the healing process. Further, braces exist that are designed to insulate the joint and restrict the movement of a joint in order to allow the body to facilitate the healing process without causing further damage to joint. However, these braces merely assist in healing a joint by stabilizing a joint or surrounding muscles. They are generally not designed to contribute to the therapeutic care or healing of an ailing joint.

While aforementioned medical devices and treatments are generally suitable for a particular purpose, such devices are not sufficiently suitable for the purpose discussed in the present invention. Thus, it is clear that there exists a need in the art for a treatment device that overcomes these problems and progresses the state of the art, as well as one that provides there additional benefits enumerated in the present application.

SUMMARY OF THE INVENTION

In view of the foregoing disadvantages inherent in the art, in accordance with a first preferred embodiment of the present invention, an apparatus for treating a joint, such as a knee decompression apparatus or device, is described. In some examples of the present invention, the apparatus is worn around the knee of a patient, and includes a bolster configured to be proximate to the popliteal fossa, or back area, of the knee. During movement of the knee, such as movement between a flexed position and a bent position, the bolster of the apparatus prevents and/or restricts normal pivoting of the top and bottom portions of a leg about the knee. This restriction facilitates a slightly different or modified pivot thereby increasing the intra-articular space of the knee while providing other inherent benefits.

The apparatus can include a bolster, one or more support bars configured to place the bolster proximate to the popliteal fossa of the knee, and one or more straps or other attachment devices configured to removably attach the apparatus to the knee (or, area of the leg that includes the knee) of a patient. The bolster can be designed of generally cylindrical shape. In some cases, the bolster is shaped or is formed of a material capable of being shaped similarly to the shape of the popliteal fossa. It is also contemplated by the present invention that the bolster is formed of multiple sub-bolsters. Furthermore, it is contemplated by the present invention that the bolster is inflatable and/or otherwise resizable, enabling a patient or care provider to modify the size of the bolster during treatment so that a single bolster design may be employed for a variety of body and joint shapes.

As mentioned, it is contemplated by the present disclosure that the bolster can be utilized in a multitude of applications, particular embodiments of the present invention can be manufactured in such a fashion as to allow for the apparatus to be worn by patients requiring a variety of various sizes and shapes, depending on joint need. In some examples, the apparatus is worn around an elbow, around one or more fingers, or around another joint of a patient. The apparatus may also be configured to facilitate the wearing and/or positioning of a bolster proximate to a back area of the joint of a patient, among other things.

Thus, in some examples, the joint decompression apparatus facilitates the widening of the intra-articular space of a patient's joint. For example, a joint decompression apparatus decompresses the meniscus of the knee, allowing for any tears in the meniscus to flatten and/or return to normal juxtaposed positions. Further, in some embodiments, the knee decompression apparatus facilitates the stretching of the patellar ligament and quadriceps tendon, which may subsequently lengthen, providing increased flexibility and/or range of motion of the knee and other areas of a patient.

Also, it is contemplated by the present invention that the joint decompression apparatus is designed to alleviate pain in patients suffering from chondromalacia (i.e. "runner's knee"), osteoarthritis, and/or other chronic ailments associated with the movement of a patient's knee or other joints. That is, in some examples, the knee decompression apparatus facilitates the adjustment or correction of affected areas (e.g., a narrowed intra-articular space) in order to assist these areas in their improvement and healing.

Thus, there has been summarized and outlined, generally in broad form, a plurality of the most important features of the present invention. While this summary is presented so that the novelty of the present contribution to the related art may be better appreciated, it will further be apparent that additional features of the invention described hereinafter (which will form the subject matter of the claims appended hereto) will further define the scope, novelty, and in certain instances the improvements upon any existing art. The following description provides specific details for a thorough understanding of, and enabling description for, various examples of the technology. One skilled in the art will understand that the technology may be practiced without many of these details and it is to be readily understood that the invention presented herein is not limited in its application to the details of construction and to the arrangements of the components set forth in the following description or illustrated in the various figures integrated and categorized herein. For example, in some instances, well-known structures and functions have not been shown or described in detail to avoid unnecessarily obscuring the description of the examples of the technology. It is intended that the terminology used in the description presented below be interpreted in its broadest reasonable manner, even though it is being used in conjunction with a detailed description of certain examples of the technology. Although certain terms may be emphasized below, any terminology intended to be interpreted in any restricted manner will be overtly and specifically defined as such in this Detailed Description section. Those skilled in the art will appreciate that the disclosure of the present invention may readily be utilized as a basis for the designing of other similar structures, methods and systems for carrying out the various purposes and objectives of the present invention. Thus, the claims as set forth shall allow for such equivalent constructions insofar as they do not depart from the spirit and scope of the present invention as described herein.

BRIEF DESCRIPTION OF THE FIGURES OF THE PRESENT INVENTION

A further understanding of the present invention and the objectives other than those set forth above can be obtained by reference to the various embodiments set forth in the illustrations of the accompanying figures. Although the illustrated embodiments are merely exemplary of the present invention, apparatus and method of use of the invention, in general, together with further objectives and advantages thereof, may be more easily understood by reference to the drawings, examples, and the following description. The examples and figures are not intended to limit the scope of this invention, which is set forth with particularity in the claims as appended or as subsequently amended, but merely to clarify and exemplify the invention. The detailed description makes reference to the accompanying figures wherein:

DETAILED DESCRIPTION OF THE PRESENT INVENTION

A detailed illustrative embodiment of the present invention is disclosed herein. However, techniques of manufacture and resulting structures in accordance with the present invention may be embodied in a wide variety of forms and modes, some of which may be quite different from those in the disclosed embodiment. Consequently, the specific structural details disclosed herein are merely representative, yet in that regard, they are deemed to afford the best embodiment for purposes of disclosure and to provide a basis for the claims herein which define the scope of the present invention. The following presents a detailed description of several examples of the present invention.

Moreover, well known methods, procedures, and substances for both carrying out the objectives of the present invention and illustrating the preferred embodiment are incorporated herein but have not been described in detail as not to unnecessarily obscure novel aspects of the present invention.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The apparatus or device ("compression apparatus") described herein is a novel device configured to decompress a patient's joint, in particular a patient's knee. The compression apparatus is designed to widen the intra-articular space of knee. Such movement of joints is widely recognized to provide many treatment benefits, such as pain alleviation, meniscus repair, increased flexibility and motion, and so on.

Figure 1:
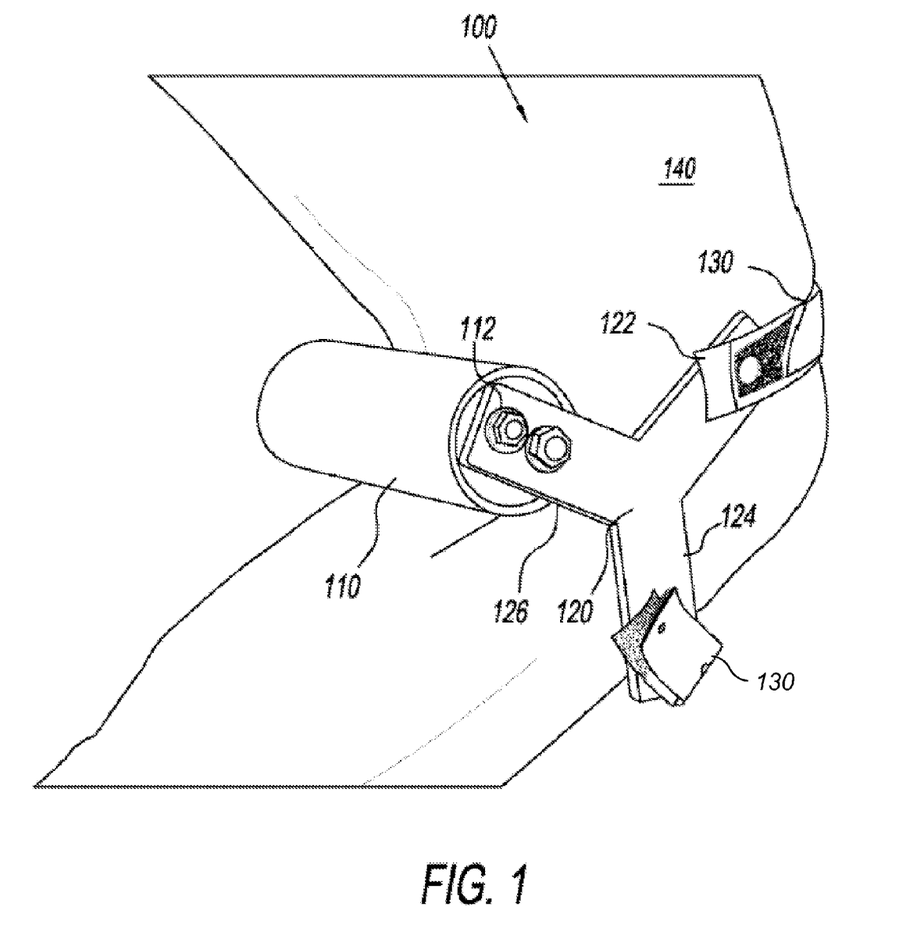
FIG. 1 is a perspective view of a knee decompression apparatus.

Turning to FIG. 1, provided is a perspective view of a knee decompression apparatus 100. The apparatus 100 includes a bolster 110, one or more support bars 120, and one or more straps 130. The bolster 110 attaches to the support bars 120 via bolts 112 or other attachment mechanisms. The straps 130 also attach to the support bars 120. In some cases, the support bars 120 are Y-shaped, having a first end 126 attached to the bolster 110 and a second end having a top portion 122 and a bottom portion 124 each attached to a strap 130.

In certain embodiments, including in the preferred embodiment, the straps 130 removably attach to the second end of the support bar 120 in order to facilitate the wearing and/or removal of the apparatus about a knee 140 by a patient, the comfort and positioning adjustment of the apparatus about the knee 140 of the patient, on the sizing of the apparatus about the knee 140 of the patient. While being worn by a patient, the bolster 110 is positioned proximate to the popliteal fossa or back area of the knee 140, the support bars are positioned and extend from the bolster 110 along the left and right sides of the knee 140 to the front of the knee, and the straps 130 extend from one support bar 120 to another. In some cases, one strap 130 extends from the top portion 122 of the support bar 120 to another, and another strap 130 extends from the bottom portion 124 of the support bar 120 to another.

In such a configuration, the movement of straps 130 positioned above and below the knee 140, such as during the bending and flexing of the knee 140, facilitate the movement of the bolster 110 towards and away from the popliteal fossa of the knee 140.

Figure 2A:
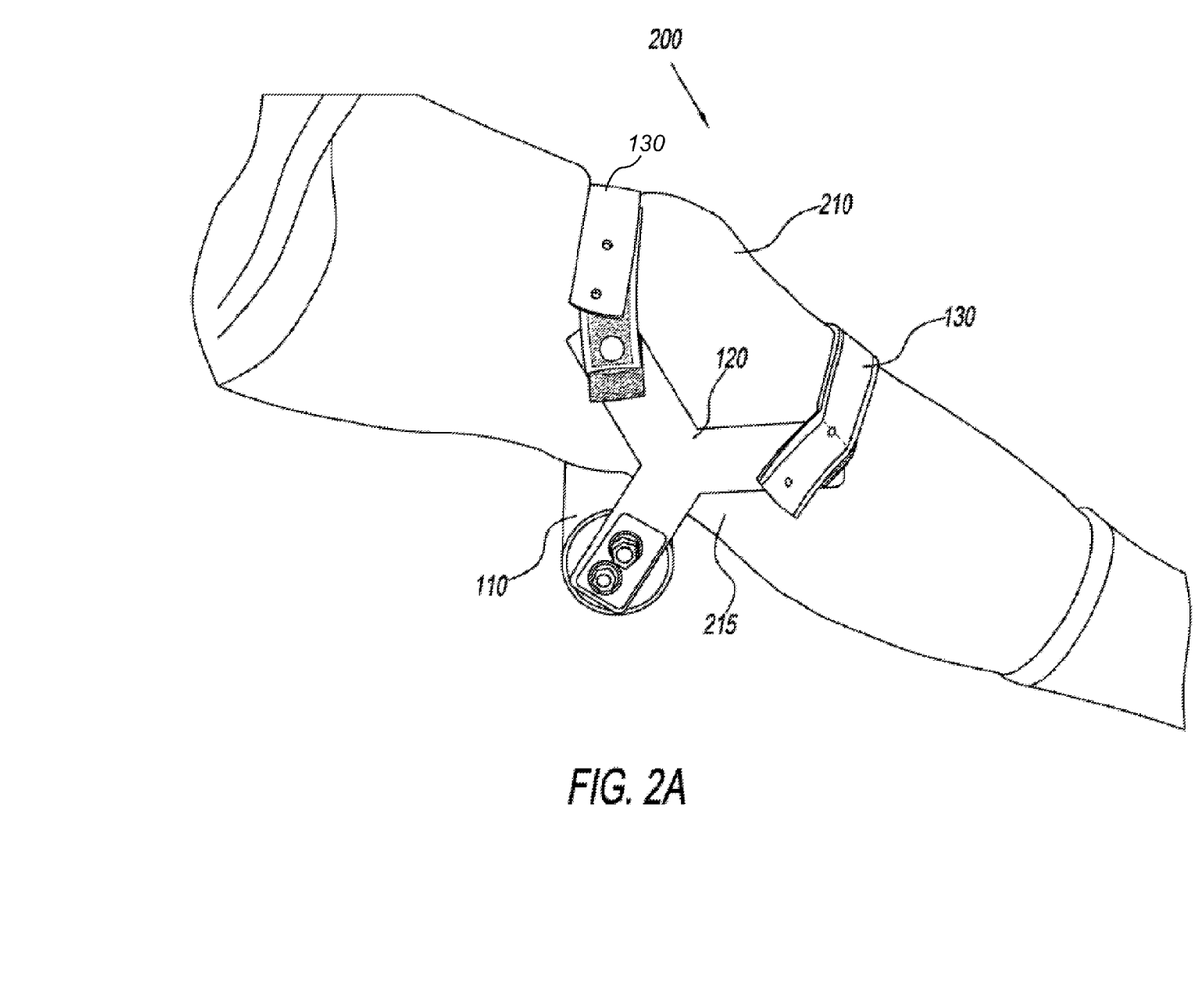
FIG. 2A is a perspective view of a knee decompression apparatus removably attached to a flexed knee.

FIG. 2A is a perspective view of a knee decompression apparatus 200 removably attached to a flexed knee 210. While the knee 210 is in a flexed position, the apparatus 200 is in a first wearable position, where the bolster 110 is proximate to the popliteal fossa 215 and, in some cases, applying pressure to the popliteal fossa 215, the patellar ligament and/or quadriceps tendon.

Figure 2B:
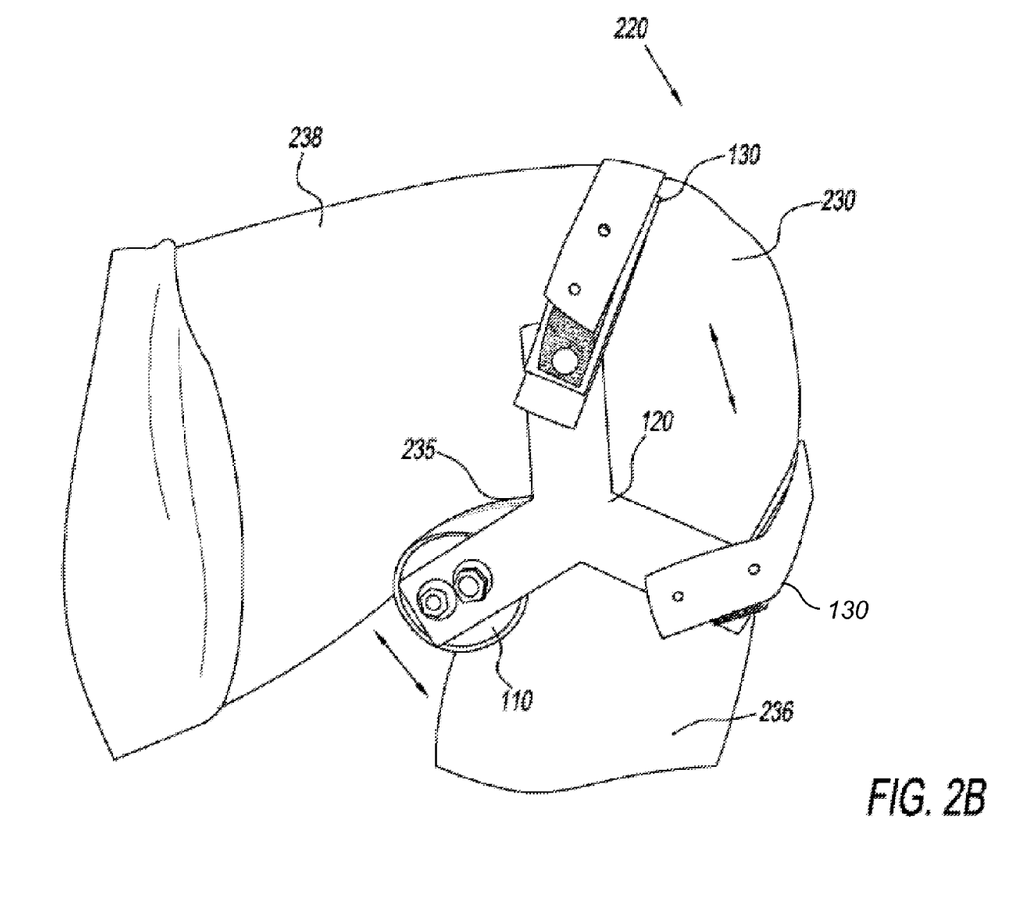
FIG. 2B is a perspective view of a knee decompression apparatus removably attached to a bent knee.

FIG. 2B is a perspective view of a knee decompression apparatus 220 removably attached to a bent knee 230. While the knee 230 is in a bent position, the apparatus 220 is in a second wearable position, where the bolster 110 is proximate to the popliteal fossa 235 and, in some cases, applying additional pressure to the popliteal fossa 215, the patellar ligament and/or quadriceps tendon. Additionally, the bending of the knee 230 around the bolster 110 may increase the intra-articular space of the knee 230 via distraction, because the bolster 110 prevents the bottom portion 236 of a leg from moving towards the top portion 238. This may cause the knee to pivot in a slightly different manner than is typical without a bolster, enabling the intra-articular space to increase.

In addition to the configurations of the knee decompression apparatus 100, 200, 220 shown in the Figures, one of ordinary skill in the art will realize that other configurations are of course possible. For example, the straps 130 may be two straps, three straps, or any number of straps that facilitate removably attaching the apparatus to a patient's knee. The straps 130 may be formed of rubber, nylon, mesh, canvas, or other materials. The straps 130 may attach to the support bars 120 by using bolts, rivets, Velcro, or other attachment devices.

Additionally, the support bars 120 may be formed in a variety of shapes, such as Y-shapes, I-shapes, or other shapes that facilitate the attachment of a bolster 110 to one end of a support bar and the attachment of one or more straps 130 to another end of the support bar. The support bars 120 may be formed of metal, plastic, or other materials.

Likewise, the bolster 110 may take on a variety of shapes and be formed of a variety of materials.

Figure 3A:
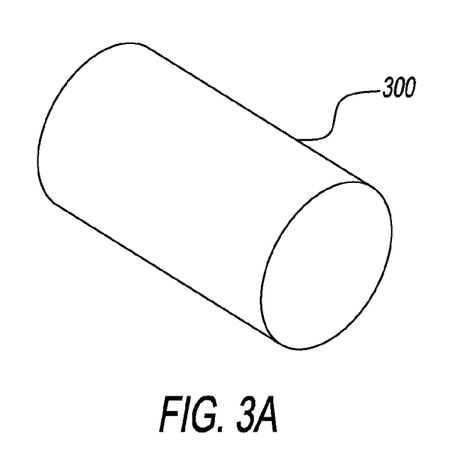
FIGS. 3A-3C are perspective views of bolsters for use with a knee decompression apparatus.
Figure 3B:
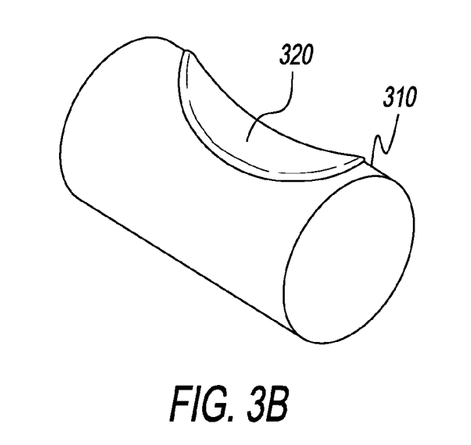
Figure 3C:
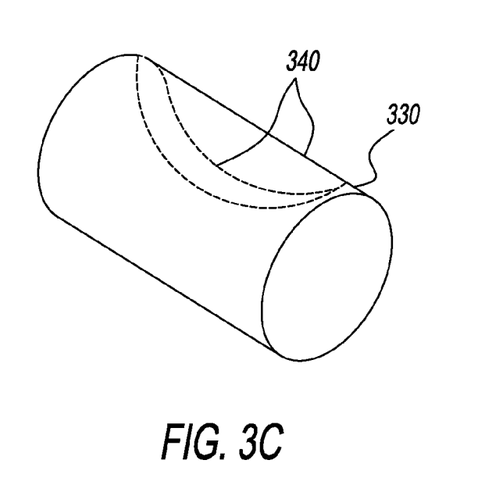

Turning to the next set of figures, FIGS. 3A-3C are perspective views of various bolsters for use with a knee decompression apparatus. Referring to FIG. 3A, a bolster 300 having a cylindrical shape, is shown. The bolster 300 may be formed in a variety of sizes based on the size of a patient, based on the comfort of a patient, based on the degree of pivot modification of the knee, based on the type of treatment, and so on. Furthermore, the bolster 300 may be formed in other shapes, such as bolsters having cross-sectional oval shapes, bolsters having cross-sectional triangle shapes, bolsters having cross-sectional rectangle shapes, bolsters having cross-sectional polygon shapes, bolsters having cross-sectional free form shapes, and so on.

Referring to FIG. 3B, a bolster 310 having a cylindrical shape and a concave contact section 320, is shown. The concave contact section 320 may be shaped similarly to the shape of a popliteal fossa of a knee. That is, the concave contact section 320 may be shaped in order to provide additional comfort to a patient during use of the knee decompression apparatus 100, to provide additional prevented movement during bending of the knee, to provide additional or less pressure to ligaments and/or tendons within the popliteal fossa, and so on.

Referring to FIG. 3C, a bolster 330 having a cylindrical shape and a conforming section 340, is shown. The conforming section 340 may be shaped similarly to the shape of a popliteal fossa of a knee by conforming to the popliteal fossa's shape during use. That is, the conforming section 320 may be take on certain shapes during use, in order to provide additional comfort to a patient during use of the knee decompression apparatus 100, to provide additional prevented movement during bending of the knee, to provide additional or less pressure to ligaments and/or tendons within the popliteal fossa, and so on.

The bolsters 300, 310, 330 shown in FIGS. 3A-3C may be formed of a number of different materials, including foam, rubber, memory foam, or other materials. Furthermore, the bolsters may include surface materials that provide additional comfort during use, such as materials that wick sweat away from the patient. Additionally, in some embodiments of the present invention, they may be formed and/or manufactured in a number of different sizes (e.g., small, medium, large) in order to fit a patient.

Figure 4A:
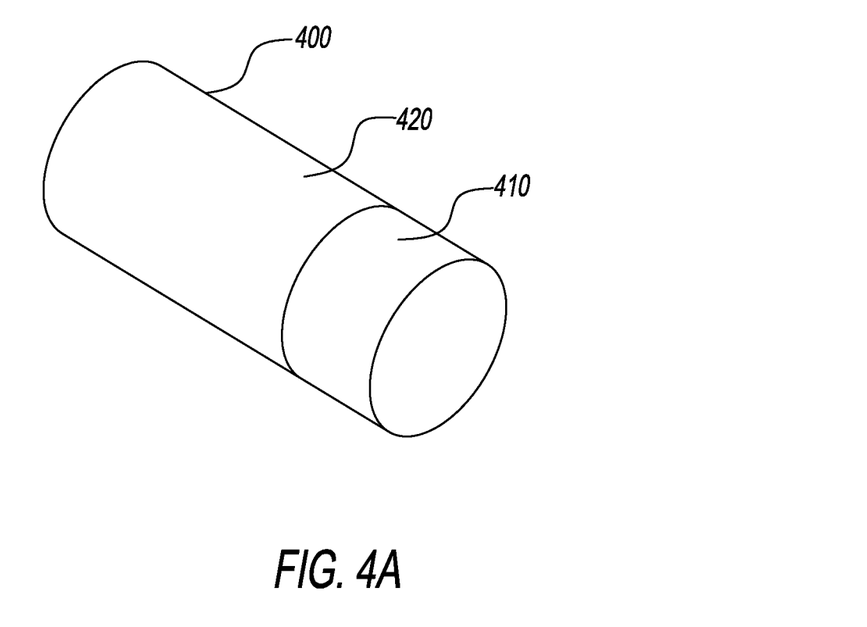
FIGS. 4A-4B are perspective views of adjustable bolsters for use with a knee decompression apparatus.

In some embodiments, the bolster 110 may be adjustable, enabling a patient or physical therapist to make adjustments to the size of the bolster during use. An example of an adjustable bolster is set for in FIG. 4A. Specifically, FIG. 4A is a perspective view of a length-wise adjustable bolster 400 for use with a knee decompression apparatus. The adjustable bolster 400 may be adjusted lengthwise (i.e., in the direction of the long axis of the cylinder). For example, a first section 410 may move away from or towards a second section 420 during a size adjustment.

Figure 4B:
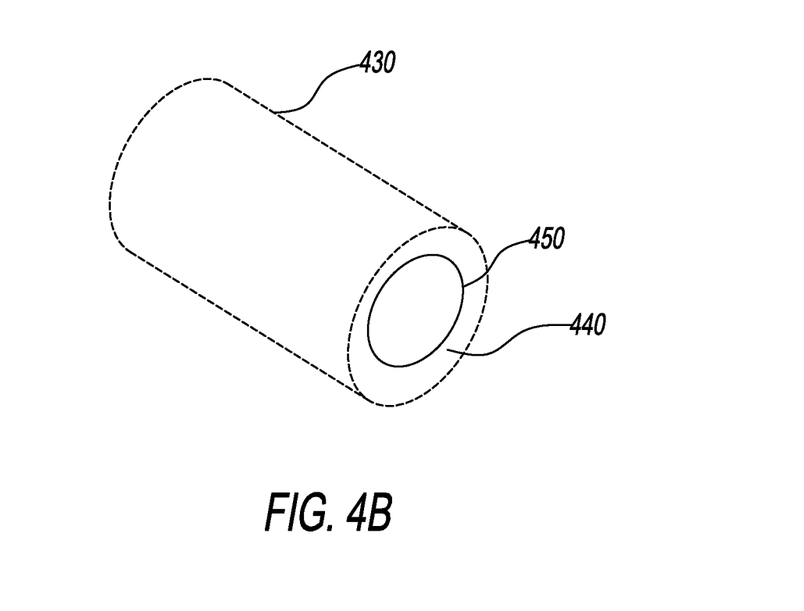

FIG. 4B is a perspective view of a width-wise adjustable bolster 430 for use with a knee decompression apparatus. The adjustable bolster 430 may include one or more removable sections 440 or coverings, that wrap around a core section 450, providing different widths of the bolster 430. Such resizing may enable patients and treatment professionals to tailor a bolster, and thus a knee compression apparatus, to the specific parameters of a patient's knee, ailment, or treatment, among other benefits.

Figures 5A, 5B, 6:
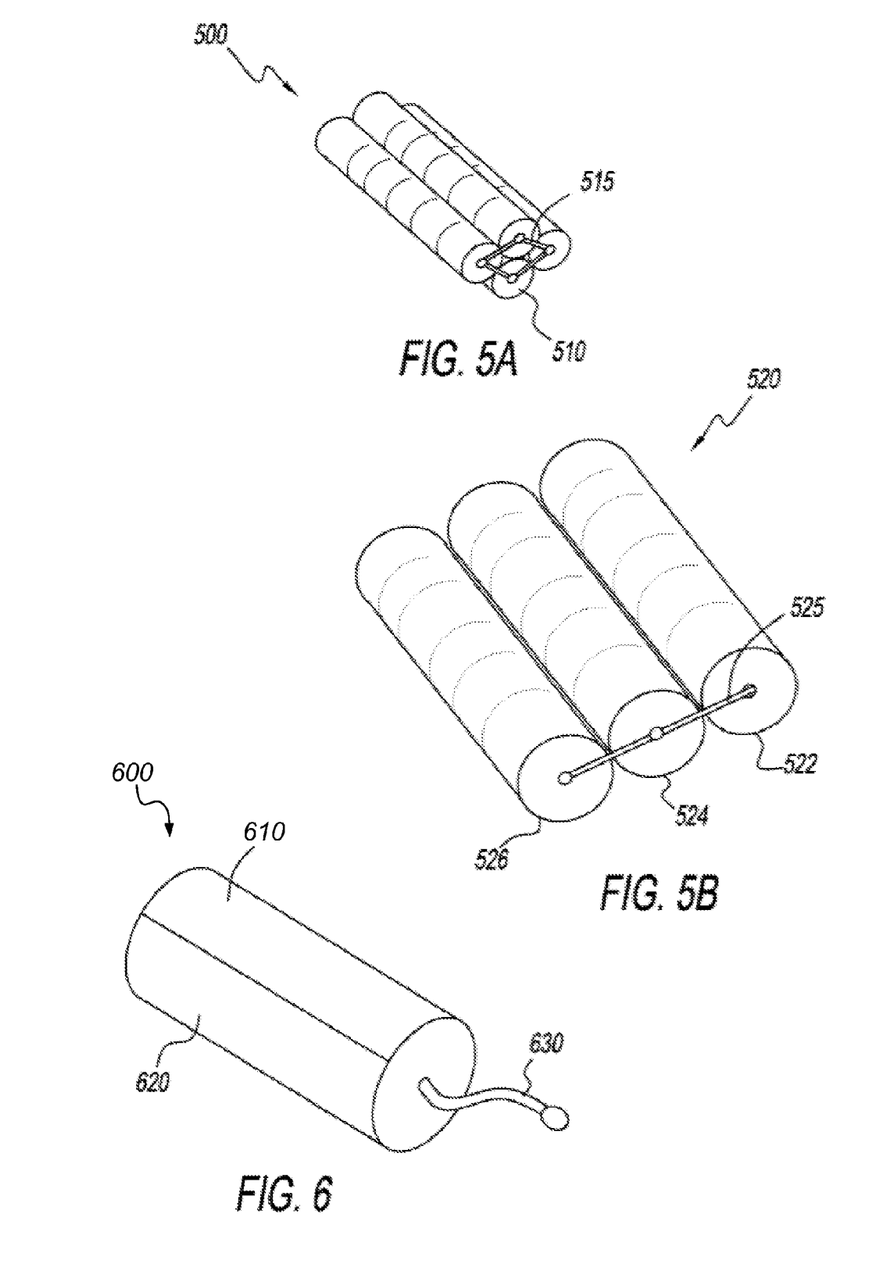
FIGS. 5A-5B are schematic diagrams illustrating bolsters having multiple components.
FIG. 6 is a schematic diagram illustrating an inflatable bolster for use with a joint decompression apparatus.

A further alternative bolster design is depicted in FIG. 5A. FIG. 5A is a perspective view of a multi-piece bolster 500 for use with a knee decompression apparatus. The bolster 500 includes two or more sub-bolsters 510, held together by a connector 515 or other attachment mechanism. In the Figure, the bolster 500 includes four sub-bolsters 510, although the bolster 500 may include more or fewer sub-bolsters 510.

The sub-bolsters 510 may be connected to one another, by the connector 515, such that they move relative to one another. For example, while a knee is bending during a treatment, the sub-bolsters 510 may move towards or away from one other. The movement may facilitate the widening of the intra-articular space of the knee or another joint via distraction, may provide additional comfort during treatment, and so on.

FIG. 5B is a perspective view of a multi-pieced bolster 520 having different sized sub-bolsters. The bolster 520 includes a small size sub-bolster 522, a medium size sub-bolster 524, and a large sub-bolster 526, held together by a connector 525. In the Figure, the bolster 520 includes three different sized sub-bolsters, although the bolster 520 may include more or few sub-bolsters with different sizes.

In some cases, the sub-bolsters 522, 524, 526 may be configured such that the small sub-bolster 522 is positioned closest to the back of a joint during a treatment, while the large sub-bolster is positioned farthest away from the back of a joint during a treatment. That is, the sub-bolsters may be configured based on the space in which they are positioned during a treatment. For example, during the treatment of a knee joint, the small sub-bolster 522 may be positioned closest to the popliteal fossa, because the space behind the knee, while the knee is bent, is smaller closer to the knee. Thus, the bolster 520 with the different sized sub-bolsters 522, 524, 526 may facilitate the widening of the intra-articular space of a knee or other joint by providing many different pivot points during a treatment, among other things.

In alternative embodiments, a patient and/or care provider may wish to adjust the size of a bolster during a treatment of a joint, such as while a knee is being treated and is in a bent position. In these instances, an inflatable bolster may be preferred as depicted in FIG. 6. FIG. 6 is a schematic diagram illustrating an adjustable bolster 600 for use with a joint decompression apparatus. The adjustable bolster 600 includes one or more inflatable sections 610, 620, and a removable pump 630. The pump facilitates the inflation and/or deflation of the inflatable sections 610, 620.

For example, during a treatment, a knee is bent around a bolster, such as bolster 600. One or more of the inflatable sections 610, 620 may then be inflated via the pump 630. The inflation may cause the bolster 600 and/or one of the sections 610, 620 to get larger, which may adjust the pressure placed to the back of the knee and/or adjusting the pivot, causing the knee to decompress in a more pronounced manner. The one or more inflatable sections 610, 620 may then be deflated, readjusting the pressure placed to the back of the knee and/or readjusting the pivot, causing the knee to return to an earlier state of decompression. Therefore, the adjustable bolster 600 may facilitate the dynamic adjustment of the amount of a joint decompression during a treatment, among other benefits.

Thus, in certain embodiments, the knee decompression apparatus as described herein facilitates a patient or physical therapist to treat an affected area of a knee. One of ordinary skill in the art will appreciate that the knee decompression apparatus may be configured to treat other joints on a patient.

Other Joint Decompression Apparatus

Figure 7:
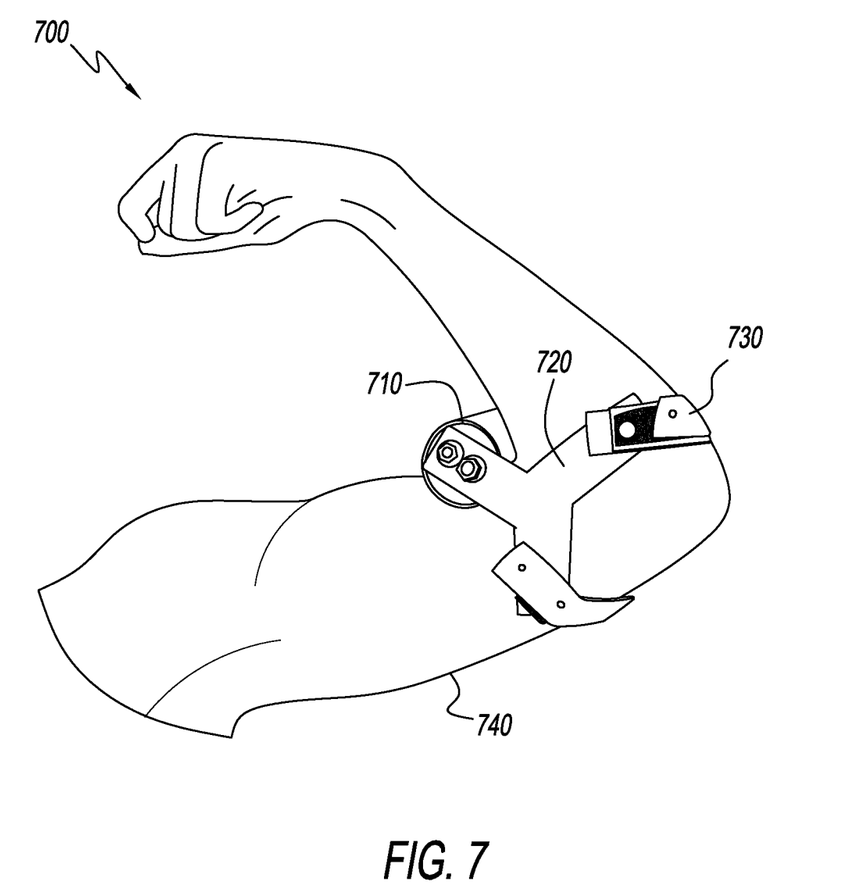
FIG. 7 is a schematic diagram of an elbow decompression apparatus removably attached to a bent elbow.

In alternative embodiments, the joint decompression devices described herein may be configured and/or fitted to other pivoting joints on a patient, such as elbow joints, finger joints, and so on. FIG. 7 is a schematic diagram illustrating an elbow decompression apparatus 700.

The elbow decompression apparatus 700 includes a bolster 710, support bars 720, and one or more straps 730 that removably attach the apparatus 700 to an elbow joint 740. As shown in the Figure, the elbow decompression apparatus 700 is attached to the elbow joint 740 such that the bolster 710 is positioned proximate to the back area of the elbow joint. When the elbow is bent during a treatment (as shown), the bolster restricts a normal bending movement, slightly altering the natural pivot of the elbow and widening the intra-articular space of the elbow via distraction, among other benefits.

The bolster 710 of the elbow decompression apparatus 700 may be similar to some or all of the bolsters described herein. In some cases, the bolster 710 may be shaped similar to bolsters 300, 310, 330. In some cases, the bolster 710 may be a bolster formed of multiple sub-bolsters, such as bolster 500 and/or bolster 520. In some cases, the bolster 710 may be an adjustable bolster, such as adjustable bolster 400 and/or bolster 600.

Figure 8A:
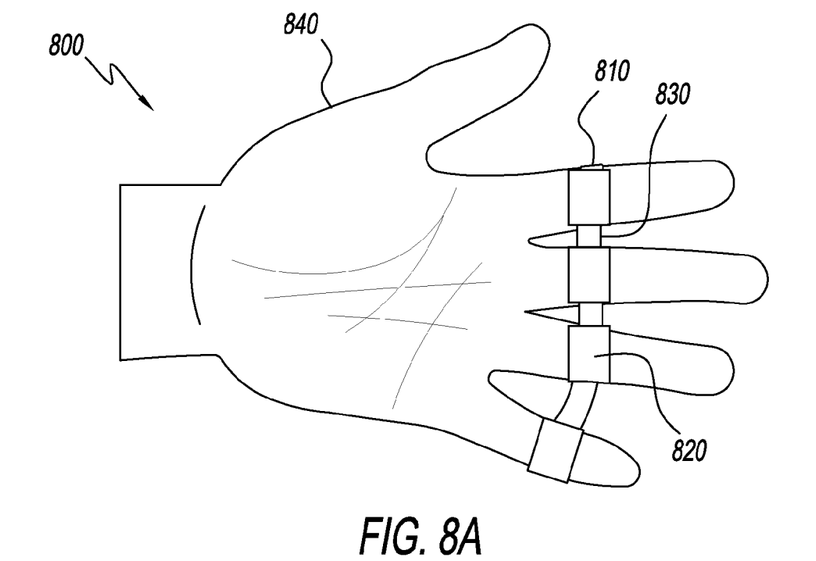
FIGS. 8A-8B are schematic diagrams of finger decompression apparatuses removably attached to fingers.

In addition to elbow joints, the joint decompression apparatus may be configured to treat finger joints on a patient. FIG. 8A is a schematic diagram illustrating a finger decompression apparatus 800. The finger decompression apparatus 800 includes a bolster 810 formed of individual finger bolsters 820 connected together by a connector 830. In some cases, the connector 830 attaches one finger bolster 820 to another while allowing for movement of the finger bolsters 820 relative to one another. The finger decompression apparatus 800 is configured to be removable attached to finger joints, such as finger joints on a hand 840. During bending of the fingers of the hand 840, such as when the hand is closed, the bolsters are positioned behind one or more of the joints of the fingers. The bolsters restrict the finger normal bending movement, slightly altering the natural pivot of the finger joints, and widening the intra-articular space of the joints via distraction, among other benefits.

Figure 8B:
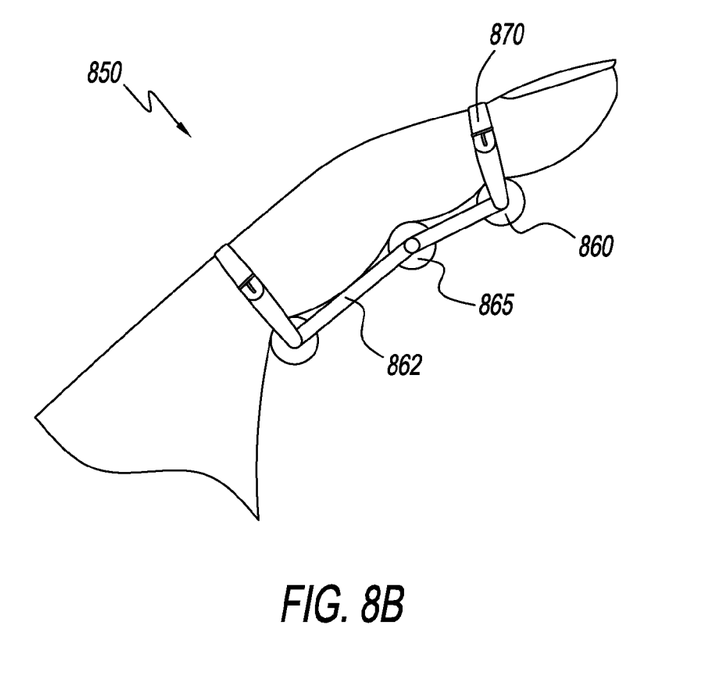

FIG. 8B is a schematic diagram illustrating a finger decompression apparatus 850 having multiple bolsters for a single finger. The finger decompression apparatus 850 includes a bolster 860 having multiple joint bolsters 865 connected together by a connector 862. For example, the bolster 860 shown in the Figure includes a joint bolster 865 for each joint of a single finger. The finger decompression apparatus 850 includes a strap 870 that removable attaches the finger decompression apparatus 850 to the finger.

The bolster 810 of finger decompression apparatus 800 and/or the bolster 860 of finger decompression apparatus 850 may be similar to some or all of the bolsters described herein.

In some cases, the bolster 810 or 860 may be shaped similar to bolsters 300, 310, 330. In some cases, the bolster 810 or 860 may be a bolster formed of multiple sub-bolsters, such as bolster 500 and/or bolster 520. In some cases, the bolster 810 or 860 may be an adjustable bolster, such as adjustable bolster 400 and/or bolster 600.

Thus, in some examples, the joint decompression apparatus may be configured for use with a knee joint, an elbow joint, a finger joint, or other pivoting joints. The joint decompression apparatus facilitates widening the intra-articular space of a joint by utilizing a bolster to restrict or modify the natural movement of a joint during a treatment, such as during the bending of the joint.

Furthermore, the joint decompression apparatus is configured to be removable attached to a patient, such as to a patient's knee, elbow, finger, or other joint. Thus, in some examples, the joint decompression apparatus includes a bolster or other pivot adjustment component, and a strap or other attachment component. Attaching the bolster proximate to an ailing joint, such as proximate to the back area of an ailing joint, enables the patient assist in his/her own care, among other benefits.

While certain aspects of the device are presented below in certain claim forms, the inventor contemplates the various aspects of the system in any number of claim forms. Accordingly, the inventor reserves the right to add additional claims after filing the application to pursue such additional claim forms for other aspects of the system.

We claim:

1. An apparatus to be worn around a joint, comprising:
a bolster, wherein a cross-sectional size of the bolster is configured to increase intra-articular joint space via distraction;
a first substantially rigid support bar connected to a first end of the bolster;
a second substantially rigid support bar connected to a second end of the bolster;
a first strap connected to the first support bar at a first upper connection and connected to the second support bar at a second upper connection; and
a second strap connected to the first support bar at a first lower connection and connected to the second support bar at a second lower connection.

2. The apparatus of claim 1,
wherein the first support bar and the second support bar are Y-shaped;
wherein the first upper connection is on a first arm of the first support bar;
wherein the second upper connection is on a first arm of the second support bar;
wherein the first lower connection is on a second arm of the first support bar;
wherein the second lower connection is on a second arm of the second support bar; and
wherein the bolster is connected to a third arm of the first support bar and a third arm of the second support bar.

3. The apparatus of claim 1, wherein the bolster is cylinder shaped.

4. The apparatus of claim 1, wherein the bolster comprises a compressible section configured to be proximate to a popliteal fossa of a knee.

5. A knee decompression apparatus, comprising:
a bolster, wherein a cross-sectional size of the bolster is configured to increase intra-articular joint space of a knee via distraction;
a first substantially rigid support bar connected to a first end of the bolster;

a second substantially rigid support bar connected to a second end of the bolster;

a first strap connecting a top portion of the first support bar to a top portion of the second support bar; and a second strap connecting a bottom portion of the first support bar to a bottom portion of the second support bar.

6. The knee decompression apparatus of claim 5, wherein the first strap extends from the top portion of the first support bar to the top portion of the second support bar above a knee cap of the knee and the second strap is configured to extend from the bottom portion of the first support bar to the bottom portion of the second support bar below the knee cap of the knee.

7. The knee decompression apparatus of claim 5, wherein the bolster is configured to be proximate to a popliteal fossa of the knee.

8. The knee decompression apparatus of claim 5, wherein the bolster is cylindrically shaped.

9. The apparatus of claim 1, wherein the first support bar is rigidly connected the first end of the bolster, and the second support bar is rigidly connected to the second end of the bolster.

10. The apparatus of claim 1, wherein the bolster comprises a concave contact section.

11. The apparatus of claim 1, wherein the bolster comprises two or more sub-bolsters.

12. The apparatus of claim 11, wherein the two or more sub-bolsters are flexibly coupled.

13. The apparatus of claim 1, wherein at least one of a size and a length of the bolster is adjustable.

14. The apparatus of claim 5, wherein the first support bar and the second support bar are Y-shaped.

15. The apparatus of claim 5, wherein the first support bar is rigidly connected the first end of the bolster, and the second support bar is rigidly connected to the second end of the bolster.

16. The apparatus of claim 5, wherein the bolster comprises a concave contact section.

17. The apparatus of claim 5, wherein the bolster comprises two or more sub-bolsters.

18. The apparatus of claim 17, wherein the two or more sub-bolsters are flexibly coupled.

19. The apparatus of claim 5, wherein at least one of a size and a length of the bolster is adjustable.

\* \* \* \* \*